United States Patent
Sugimoto et al.

(10) Patent No.: US 7,567,238 B2
(45) Date of Patent: Jul. 28, 2009

(54) METHOD FOR SUPPORTING MEDICAL TREATMENT SYSTEM AND MEDICAL TREATMENT SUPPORT SYSTEM

(75) Inventors: Mamiko Sugimoto, Osaka (JP); Takeo Igarashi, Kanagawa (JP); Kazuo Nakazawa, Osaka (JP); Takashi Ashihara, Shiga (JP)

(73) Assignee: NEC Corporation, Tokyo (JP)

( * ) Notice: Subject to any disclaimer, the term of this patent is extended or adjusted under 35 U.S.C. 154(b) by 697 days.

(21) Appl. No.: 09/989,437

(22) Filed: Nov. 21, 2001

(65) Prior Publication Data

US 2002/0060702 A1    May 23, 2002

(30) Foreign Application Priority Data

Nov. 22, 2000   (JP) .............................. 2000-356372

(51) Int. Cl.
 G06F 3/041  (2006.01)
 G06F 3/033  (2006.01)
(52) U.S. Cl. ........................................ 345/173; 345/179
(58) Field of Classification Search ......... 345/173–179; 715/863; 711/161–162; 707/203–204
 See application file for complete search history.

(56) References Cited

U.S. PATENT DOCUMENTS

| | | | | | |
|---|---|---|---|---|---|
| 5,249,296 | A | * | 9/1993 | Tanaka ........................ | 715/799 |
| 5,454,371 | A | * | 10/1995 | Fenster et al. ................ | 600/443 |
| 5,561,446 | A | * | 10/1996 | Montlick ..................... | 345/173 |

(Continued)

FOREIGN PATENT DOCUMENTS

JP    63-140332    6/1988

(Continued)

OTHER PUBLICATIONS

Elizabeth Mynatt, Takeo Igarashi, W. Keith Edwards, and Anthony LaMarca,"Flatland: New Dimensions in Office Whiteboards", CHI'99, Proceedings of the SIGCHI conference on Human factors in computing systems, 1999, pp. 346-353.*

(Continued)

*Primary Examiner*—Bipin Shalwala
*Assistant Examiner*—Steven E Holton
(74) *Attorney, Agent, or Firm*—McGinn IP Law Group, PLLC

(57) ABSTRACT

A medical treatment support system has operations A to G on a display screen to easily handle respective data on a sheet. Operation A facilitates the browsing of a large amount of data. Operations B and C allow the user to easily copy and move data. Operation D is a scale function to facilitate measurement. Using operation E, the operator can easily divide an area into segments only by drawing a horizontal line. Operation F is used to change a display angle of image data displayed on the screen. Operation G allows the user to browse respective data classified for each sheet label. The new functions of the single-unit input/output pen-tablet device can be intuitively operated by a user not versed in the functions. This consequently mitigates the load of complex input operation which interrupts thinking of the user and which hinders diagnosis mitigated in medical treatment. A medical treatment support system, a display method for the same, and a recording medium having stored the same provide, in the processing of information regarding medical treatment, advantages of electronic data processing and advantages of processing of handwritten data on a sheet of paper.

35 Claims, 10 Drawing Sheets

U.S. PATENT DOCUMENTS

| | | | | |
|---|---|---|---|---|
| 5,572,651 | A | * | 11/1996 | Weber et al. ................. 715/863 |
| 5,583,946 | A | * | 12/1996 | Gourdol ...................... 382/187 |
| 5,724,985 | A | * | 3/1998 | Snell et al. .................. 600/510 |
| 5,737,740 | A | * | 4/1998 | Henderson et al. ........... 715/530 |
| 6,055,506 | A | * | 4/2000 | Frasca, Jr. ...................... 705/3 |
| 6,098,084 | A | * | 8/2000 | Mori ........................... 715/526 |
| 6,457,883 | B1 | * | 10/2002 | Silverbrook et al. .......... 400/62 |

FOREIGN PATENT DOCUMENTS

| | | |
|---|---|---|
| JP | 6-178 | 1/1994 |
| JP | 6-162120 | 6/1994 |
| JP | 6-243177 | 9/1994 |
| JP | 6-337862 | 12/1994 |
| JP | 8-147138 | 6/1996 |
| JP | 8-194756 | 7/1996 |
| JP | 8-241159 | 9/1996 |
| JP | 9-245063 | 9/1997 |
| JP | 10-214302 | 8/1998 |
| JP | 10-275106 | 10/1998 |
| JP | 10-309324 | 11/1998 |
| JP | 11-31187 | 2/1999 |
| JP | 11-045304 | 2/1999 |
| JP | 11-86010 | 3/1999 |
| JP | 11-259459 | 9/1999 |
| JP | 11-353405 | 12/1999 |
| JP | 3066658 | 12/1999 |
| JP | 2000-163193 | 6/2000 |
| JP | 2000-181606 | 6/2000 |
| JP | 2000-242390 | 9/2000 |
| JP | 2000-276550 | 10/2000 |

OTHER PUBLICATIONS

Takeo Igarshi, W. Keith Edwards, Anthony LaMarca, and Elizabeth D. Mynatt, "Software Architecture Based on Free Strokes for Pen-Based Interaction On Electronic Whiteboards", Interaction 2000, Tokyo Institute of Technology, Mar. 2000, 8 pages with ABS.*

Takeo Igarashi, W. Keith Edwards, Anthony LaMarca and Elizabeth D. Mynatt, "Software Architecture Based on Free Strokes for Pen-Based Interaction On Electronic Whiteboards", Interaction 2000, Tokyo Institute of Technology, Mar. 2000, 8 pages with ABS.

Takeo Igarashi, Takashi Ashihara, Satoru Nagata, Masahiro Takada and Kazuo Nakazawa, "A Pen-based Interface for Electronic Medical Recording System: Toward Stress-free Experience for Doctors",Information Engineering Dept., The University of Tokyo, First Dept. of Internal Medicine, Dept. of Ophthalmology, Shiga University of Medical Science Dept. of Pharmacy, Research Institute, National Cardiovascular Center.

Japanese Office Action dated Sep. 21, 2004, with partial English translation.

"Medical Treatment and Computers", Corporate Japan Electronic Publications, Jun. 20, 1997, vol. 8, No. 2, pp. 17-21.

"Electronic Record-keeping Changes Medical Treatment", Nikkei BP Co., Ltd., Nov. 9, 1998, pp. 225-227.

* cited by examiner

F I G. 7
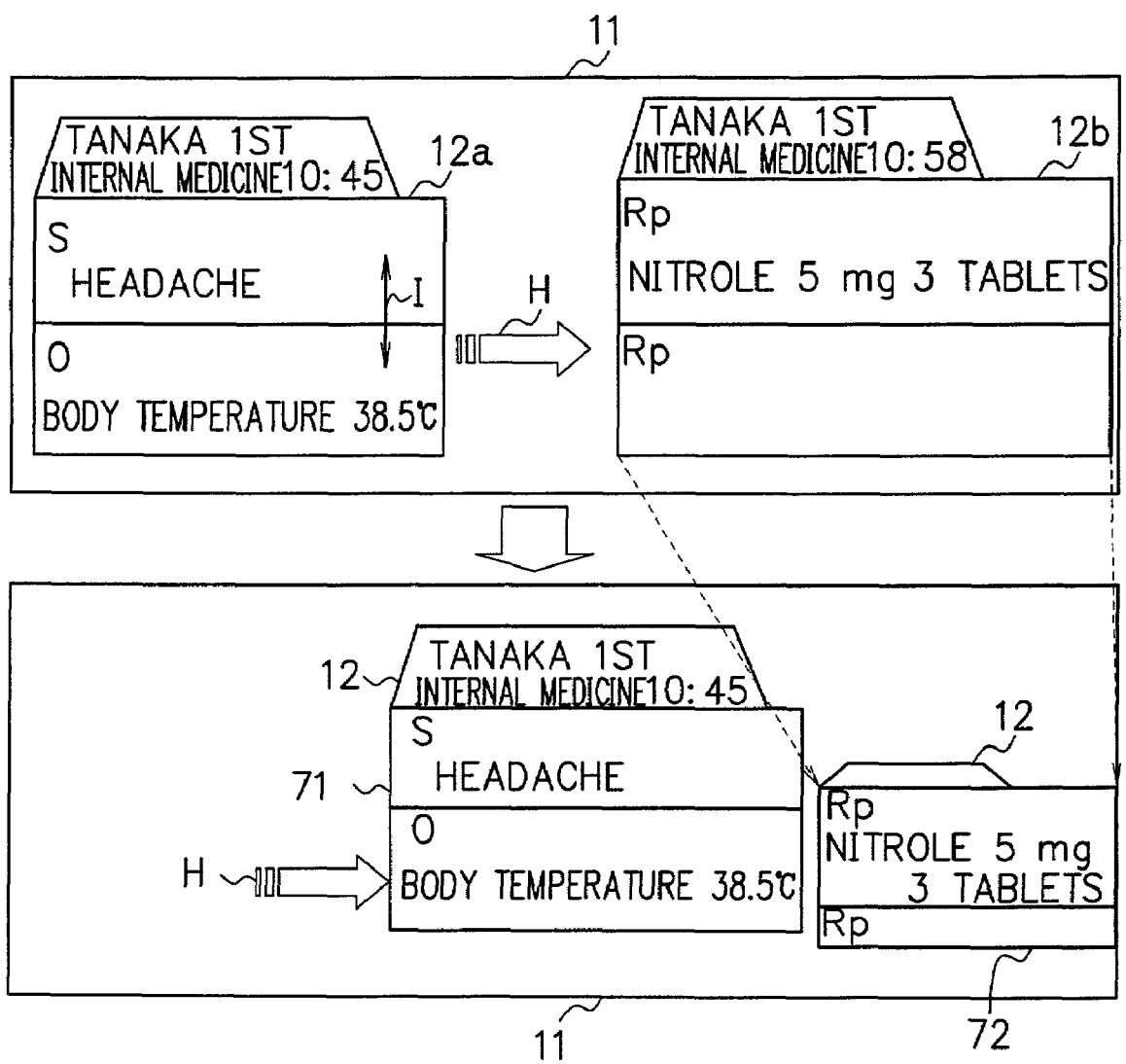

METHOD FOR SUPPORTING MEDICAL TREATMENT SYSTEM AND MEDICAL TREATMENT SUPPORT SYSTEM

BACKGROUND OF THE INVENTION

The present invention relates to a method for supporting a medical treatment system and a medical treatment support system, and in particular to a method for supporting a medical treatment system and a medical treatment support system for use with an electronic medical report, an ordering system and the like regarding medical treatment.

DESCRIPTION OF THE PRIOR ART

Heretofore, information of medical treatment is written by hand on a sheet of paper, which is advantageously flexible. For example, a free handwritten note can be taken, a copy of necessary information can be fixed onto the sheet of paper, a drawing of a fixed pattern can be fixed thereonto, and a note can be made thereon. Furthermore, important items and contents can be underlined and/or marked on the sheet of paper. Additionally, a tag can be fixed onto the sheet of paper and accumulated sheets of paper for the notes of medial treatment can be stored in colored files according to classifications thereof. The stored information can be visually identified for convenience of management thereof. A large amount of information can also be easily browsed.

However, it has been known that the sheet of paper used to record the medical treatment is attended with drawbacks, for example, possibility of destruction thereof, difficulty to reserve a place to store the sheets of paper, and difficulty of retrieval thereof. To solve these problems, the documents in the form sheets of paper such as the medical report and the recipe are increasingly converted into electronic data or information at present.

The electronic system of the medical documents has advantages that the data is not destroyed like the sheet of paper, the data is stored and is managed or controlled in a unified manner for shared uses, and a keyword retrieval is possible for a large amount of data. Moreover, this improves the problems of a high cost and a large storage area to store the information of medical treatment such as the sheets of medical reports.

However, also in the electronic medical treatment system, complex operations are required for various useful functions. Operations to input data from a keyboard or the like during a medical treatment of a patient impose a considerable load on the doctor or the like onto the user or operator. The load hinders ordinary thinking of the user, and it takes a long period of time to master the input operations. In contrast therewith, the input method using a pen-tablet device allows the user to input data of medical treatment in an easy operation with a feeling similar to that of the operation of the prior art in which the user writes a medical report by hand. Any operator can easily input data of medical treatment in the usual handwriting operation using the pen.

Japanese Patent Laid-Open No. HEI 10-214302 describes an example of a medical treatment support system using a pen-tablet device of the prior art. Reference is to be made to description of an input pen and an input tablet in page 8 and a drawing of an input device and an output device in page 14 of "Medical Treatment Support System" issued from the Kameda Medial Information Institute in 1988.

FIG. 13 shows an outline of the configuration of a medical treatment support system 130 using an input pen and an input tablet of the prior art. The system 130 of FIG. 13 includes a storage 131, an input device 132, a controller 133, a communication device 34, a printer 135, and a display 136. The medical treatment support system 130 using the pen-tablet device of the prior art operates as follows.

The operator visually confirms the contents presented on the display 136 to determine a subsequent operation. When the next operation uses, for example, a mouse, the operator changes the setting of the input device 132 to a mouse for the operation. When the next operation is a text input, the operator changes the setting of the input device 132 to a keyboard, an input pen, or an input tablet for the operation. During the operation, the operator confirms that the contents inputted from the input device 132 are substantially equal to those displayed on the display 136.

Furthermore, an example of the software architecture based on free strokes of the prior art is described in pages 213 to 220 of the "A Software Architecture Based on Free Strokes for Pen-Based Interaction On Electronic Whiteboards" written by Takeo Igarashi, W. Keith Edwards, Anthony LaMarca, and Elizabeth D. Mynatt published in the Interaction 2000 held in March 2000 at Tokyo Institute of Technology.

The electronic whiteboard system of the prior art using the software architecture based on free strokes manages history as below. History of strokes is stored in a database. Each time a user operation is started, a transaction start mark is stored in the history. Each time a user operation is finished, a transaction end mark is stored in the history. The history, viewed from the user side, includes local history associated with a particular segment and global history associated with the overall screen. The history is managed for each segment, and the global history is dynamically constructed by automatically combining history of segments with each other. Moreover, history regarding rewriting of data structure unique to an application processing module can be ignored and only the history regarding the rewriting of segment strokes are to be handled or processed. Therefore, the reproduction or playback operation can be conducted at a high speed without using the application processing module.

However, the medical treatment support system described above is attended with problems as follows.

First, the complex specifications operations of the system interrupts the thinking of the operator (doctor, or medicine), and hence hinders the medical diagnosis. Specifically, the system operations based on selections of menus and buttons are required. That is, knowledge of the complex specifications is required for the operations. To master the operation method requires a long period of time. Consequently, there disadvantageously occurs a case in which the operator must search for an appropriate operation while conducting an input operation.

Second, the change of the display screen interrupts the thinking of the medicine (operator), which hinders the medical diagnosis. The display size of the screen is limited in the display. Therefore, to display a large amount of information, the screen image must be changed.

Third, the input operation interrupts the thinking of the medicine (operator), which hinders the medical diagnosis. When the operator is not versed in operation of the keyboard using the blind-touch operation, the operator repeatedly conducts the input operation and the confirmation thereof using the input devices such as the keyboard, the input pen, and the input tablet.

Fourth, the input device is apart from the display for the input device and the display are two parts and hence there exists a spatial difference between the eyes and the hands. This increases the input load and hence hinders the medical diagnosis. This is because the input devices such as the keyboard, the input pen, and the input tablet are not integrally unified with the display.

Fifth, the input devices are changed according to the input contents. This is because the input operations cannot be conducted only by one kind of the input device when the input devices of the prior art such as a keyboard, a ten-key switch, a mouse, a track ball, an input pen, and an input tablet are used.

Sixth, while the data management of information regarding the mental treatment is basically conducted for each patient, the data management of free strokes is to be conducted for each operation user for the following reasons. Data must be collected for each user operation so that the user conducts UNDO/REDO and trace time-series data.

SUMMARY OF THE INVENTION

It is therefore an object of the present invention, which has been devised to solve the problems, to provide a medical treatment support system, an application for supporting the medical treatment system, and a program for applying the system regarding medical treatment, a remarkable advantage through the standardization and the electronic storage and management and an advantage of the paper system in which results of medical treatment are handwritten on sheets of paper.

To achieve the objects above in accordance with the present invention, there is provided an application method for medical treatment system comprising an input/display device including input means and display means, a storage, a printer, a communication device; and a controller, wherein in a first operation in which said input means is moved in a sliding manner on each of sheet labels displayed at particular positions on a screen by said display means, said input/display device reads, when said input means moves onto each said sheet label, data stored in said storage in relation to said each sheet label from said storage and then displays the data by conducting a change-over operation for said each sheet label.

According to the application method for medical treatment system, further comprising the input means drags a particular input field selected from a plurality of input fields displayed at particular positions on a screen by said display means and then drops the particular input field onto said sheet label, said storage stores data of said particular input field with a relationship established to said sheet label.

According to the application method for medical treatment system, in a third operation in which said input means is moved in a horizontal direction in a sliding manner to cross an input field displayed at a particular position on a screen by said display means, said input/display device displays said input field after said third operation, said input field being subdivided into segments.

According to the application method for medical treatment system, when the segments of said input field are displayed, segment labels are assigned to the segments according to sequence numbers beforehand specified to the respective segments.

According to the application method for medical treatment system, in a fourth operation in which said input means drags a segment selected from the segments of the input field displayed at particular positions on a screen by said display means and then drops the particular segment onto said sheet label, said storage stores data of said particular segment with a relationship established to said sheet label.

According to the application method for medical treatment system, in a fifth operation in which said input means is moved from a first particular point to a second particular point on an image displayed at a particular position on a screen by said display means, said input/display device measures a distance of movement between the first and second particular points and displays the distance over said image in an overlapping manner.

According to the application method for medical treatment system, in a sixth operation in which said input means is moved to draw an arc beginning at a particular point on an image displayed at a particular position on a screen by said display means, said input/display device rotates said image according to a length and a direction of said arc and then displays said image.

According to the application method for medical treatment system, in a seventh operation in which said input means drags a particular input field selected from a plurality of input fields displayed at particular positions on a screen by said display means and moves said particular input field in said screen, said input/display device minimizes or magnifies said particular input field or other input fields on the screen according to the movement of said particular input field dragged by said input means.

According to the application method for medical treatment system, in an eighth operation in which said input means drags a particular segments of the segments of the input field displayed at particular positions on a screen by said display means and moves said particular segment in said screen, said input/display device minimizes or magnifies said particular segment or other segments on the screen according to the movement of said particular segment dragged by said input means.

According to the application method for medical treatment system, in a ninth operation in which said input means drags a particular sheet label selected from a plurality of sheet labels displayed at particular positions on a screen by said display means and then moves said particular sheet label upward, said input/display device reads data stored in said storage in relation to said each sheet label from said storage and displays the data below said each sheet label by classifying said data.

According to the application method for medical treatment system, said input/display device conducts character recognition processing for handwritten data inputted from said input means, the handwritten data being an array of values of coordinates; converts by said character recognition processing the data into text data including an array of character codes, and displays the text data.

According to the application method for medical treatment system, in the operation to read data from said storage and to display the data, when an unchangeable state is beforehand set to the data, said input/display device displays an item indicating that the data cannot be changed.

According to the application method for medical treatment system, wherein said input/display device is a pen-tablet device.

According to the application method for medical treatment system, said pen-tablet device is a pen-tablet device including a cordless pen.

According to the application method for medical treatment system, said display means is a liquid-crystal display.

According to the application method for medical treatment system, said controller comprises storage data update control means for updating data to be stored in said storage; display data generation control means for generating data to be displayed on said display means or said other display means; and print data generation control means for generating data to be printed on a sheet of paper by said printer.

According to application method for medical treatment system, said display data control means controls operation in which data to be displayed on said display means is different from data displayed on the other display means.

In accordance with the present invention, there is provided a medical treatment support system comprising an input/display device including input means and display means, a storage, a communication device; and a controller, wherein;

the input/display device inputted by handwriting and the storage stored substantially all as medical data.

In the system it is preferred that the medical treatment support system wherein the storage is substantially all stored after depression of a Lock button or an operation to explicitly close a medical report.

Furthermore, in the system it is preferred that a medical treatment support system comprising an input/display device including input means and display means; a storage; a printer; a communication device; and a controller, wherein in a first operation. Said input means is moved in a sliding manner on each of sheet labels displayed at particular positions on a screen by said display means, said input/display device reads, when said input means moves onto each said sheet label, data stored in said storage in relation to said each sheet label from said storage and then displays the data by conducting a change-over operation for said each sheet label.

And the system is used preferably that the input means drags a particular input field selected from a plurality of input fields displayed at particular positions on a screen by said display means and then drops the particular input field onto said sheet label, said storage stores data of said particular input field with a relationship established to said sheet label.

And the system is used preferably that the input means is moved in a horizontal direction in a sliding manner to cross an input field displayed at a particular position on a screen by said display means, said input/display device displays said input field after said third operation, said input field being subdivided into segments.

And the system is used preferably when the segments of said input field are displayed, segment labels are assigned to the segments according to sequence numbers beforehand specified to the respective segments.

And the system is used preferably that the input means drags a segment selected from the segments of the input field displayed at particular positions on a screen by said display means and then drops the particular segment onto said sheet label, said storage stores data of said particular segment with a relationship established to said sheet label.

And the system is used preferably that the input means is moved from a first particular point to a second particular point on an image displayed at a particular position on a screen by said display means, said input/display device measures a distance of movement between the first and second particular points and displays the distance over said image in an overlapping manner.

And the system is used preferably that the input means is moved to draw an arc beginning at a particular point on an image displayed at a particular position on a screen by said display means, said input/display device rotates said image according to a length and a direction of said arc and then displays said image.

And the system is used preferably that the input means drags a particular input field selected from a plurality of input fields displayed at particular positions on a screen by said display means and moves said particular input field in said screen, said input/display device minimizes or magnifies said particular input field or other input fields according to the movement of said particular input field dragged by said input means.

And the system is used preferably that the input means drags a particular segments of the segments of the input field displayed at particular positions on a screen by said display means and moves said particular segment in said screen, said input/display device minimizes or magnifies said particular segment or other segments according to the movement of said particular segment dragged by said input means.

And the system is used preferably that the input means drags a particular sheet label selected from a plurality of sheet labels displayed at particular positions on a screen by said display means and then moves said particular sheet label upward, said input/display device reads data stored in said storage in relation to said each sheet label from said storage and displays the data below said each sheet label by classifying said data.

And the system is used preferably that the input/display device conducts character recognition processing for handwritten data inputted from said input means, the handwritten data being an array of values of coordinates; converts by said character recognition processing the data into text data including an array of character codes, and displays the text data.

Furthermore, the system is used preferably at least one selected from;

in the operation to read data from said storage and to display the data, when an unchangeable state is beforehand set to the data, said input/display device displays an item indicating that the data cannot be changed;

the medical treatment support system, said input/display device is a pen-tablet device, the pen-tablet device is a pen-tablet device including a cordless pen;

the display means is a liquid-crystal display;

the medical treatment system includes other input means;

the medical treatment system includes display means;

the controller comprises storage data update control means for updating data to be stored in said storage; display data generation control means for generating data to be displayed on said display means or said other display means; and print data generation control means for generating data to be printed on a sheet of paper by said printer; and the display data control means controls operation in which data to be displayed on said display means is different from data displayed on the other display means.

In accordance with the present method is preferably executed by using a program of a medical treatment support system comprising an input/display device including input means and display means, a storage, a printer, a communication device; and a controller, wherein in a first operation in which said input means is moved in a sliding manner on each of sheet labels displayed at particular positions on a screen by said display means, there are executed processing, when said input means moves onto each said sheet label, to read data stored in said storage in relation to said each sheet label from said storage; and processing to display, on said input/display device, the data by conducting a change-over operation for said each sheet label.

And the program is contained preferably that the input means drags a particular input field selected from a plurality of input fields displayed at particular positions on a screen by said display means and then drops the particular input field onto said sheet label, there is executed processing to store, in said storage, data of said particular input field with a relationship established to said sheet label.

And the program is contained preferably that the input means is moved in a horizontal direction in a sliding manner to cross an input field displayed at a particular position on a screen by said display means, there is executed processing to display, on said input/display device, said input field after said third operation, said input field being subdivided into segments.

And the program is contained preferably that the input field are displayed, segment labels are assigned to the segments according to sequence numbers beforehand specified to the respective segments.

And the program is contained preferably that the input means drags a segment selected from the segments of the input field displayed at particular positions on a screen by said display means and then drops the particular segment onto said sheet label, there is executed processing to store, in said storage, data of said particular segment with a relationship established to said sheet label.

And the program is contained preferably that the input means is moved from a first particular point to a second particular point on an image displayed at a particular position on a screen by said display means, a distance of movement between the first and second particular points is measured and the distance is displayed on said input/display device over said image in an overlapping manner.

And the program is contained preferably that the input means is moved to draw an arc beginning at a particular point on an image displayed at a particular position on a screen by said display means, said image is rotated according to a length and a direction of said arc and then said image thus rotated is displayed on said input/display device.

And the program is contained preferably that the input means drags a particular input field selected from a plurality of input fields displayed at particular positions on a screen by said display means and moves said particular input field in said screen, said particular input field or other input fields is or are minimized or magnified according to the movement of said particular input field dragged by said input means and an image resultant from the minimization or magnification is displayed on said input/display device.

And the program is contained preferably that the input means drags a particular segments of the segments of the input field displayed at particular positions on a screen by said display means and moves said particular segment in said screen, said particular segment or other segments is or are minimized or magnified on the screen according to the movement of said particular segment dragged by said input means and an image resultant from the minimization or magnification is displayed on said input/display device.

And the program is contained preferably that the input means drags a particular sheet label selected from a plurality of sheet labels displayed at particular positions on a screen by said display means and then moves said particular sheet label upward, data stored in said storage in relation to said each sheet label is read from said storage and is displayed below said each sheet label on said input/display device by classifying said data.

And the program is contained preferably that the program conducts character recognition processing for handwritten data inputted from said input means, the handwritten data being an array of values of coordinates, and converts by said character recognition processing the data into text data including an array of character codes and displays the text data on said input/display device.

Furthermore, the system is used the program preferably further comprising at least one selected from;

in the operation to read data from said storage and to display the data, when an unchangeable state is beforehand set to the data, an item indicating that the data cannot be changed is displayed on said input/display device;

the input/display device is a pen-tablet device;

the pen-tablet device is a pen-tablet device including a cordless pen;

the display means is a liquid-crystal display;

the controller executes storage data update control processing of updating data to be stored in said storage; display data generation control processing of generating data to be displayed on said display means or said other display means; and print data generation control processing of generating data to be printed on a sheet of paper by said printer; and the display data control processing makes data to be displayed on said display means be different from.

BRIEF DESCRIPTION OF THE DRAWINGS

The objects and features of the present invention will become more apparent from the consideration of the following detailed description taken in conjunction with the accompanying drawings in which:

FIG. 7 is a diagram showing a third display example of the input/display device used in the embodiment in accordance with the present invention;

DESCRIPTION OF THE EMBODIMENTS

Referring next to the accompanying drawings, description will be given in detail of a medical treatment support system in an embodiment in accordance with the present invention, a display method of the same, and a program for supporting a medical treatment system. FIGS. 1 to 12 show embodiments of a medical treatment system in accordance with the present invention, a display method of the same, and a program for supporting the medical treatment system.

First Embodiment

Figure 1:
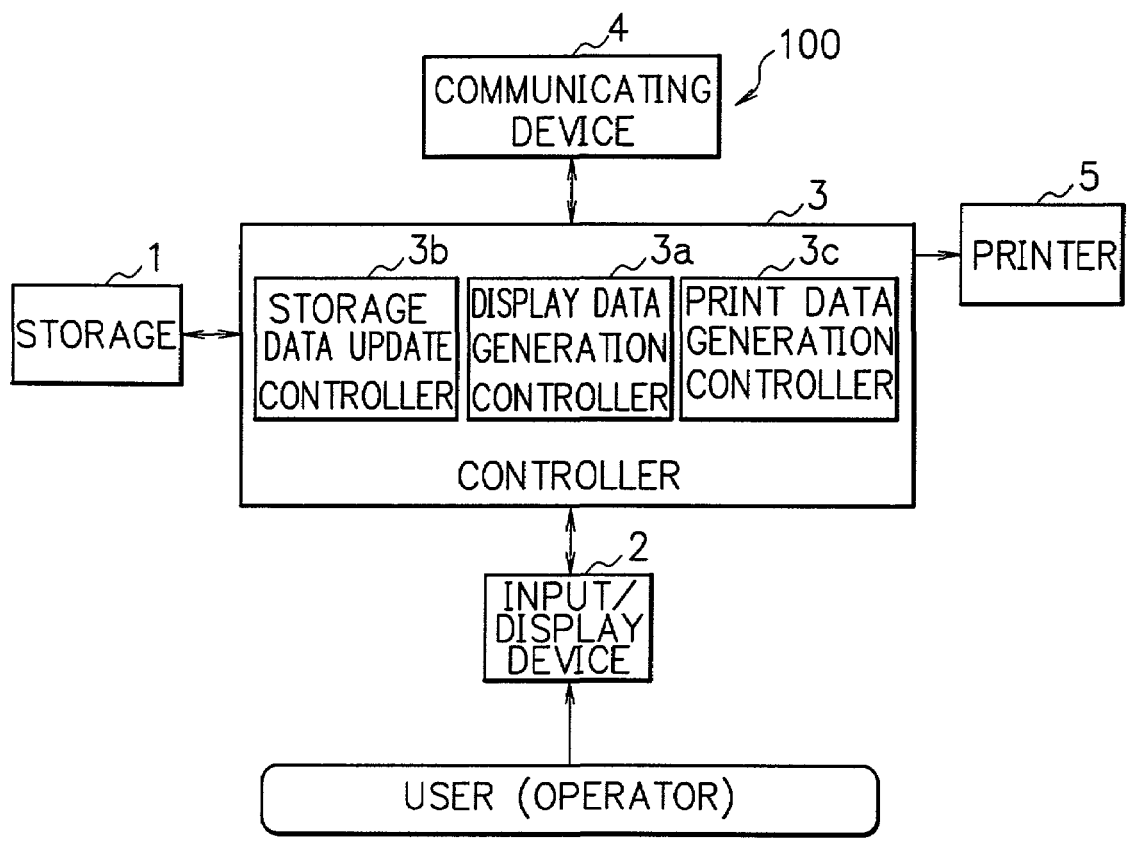
FIG. 1 is a block diagram showing an outline of the configuration of a first embodiment of a medical treatment support system in accordance with the present invention.

FIG. 1 shows an outline of the configuration of a first embodiment of a medical treatment support system in accordance with the present invention in a block diagram. In FIG. 1, a medical treatment support system 100 includes a storage 1, an input/display device 2, a controller 3, a communication device 4, and a printer 5.

In comparison with the medical treatment support system of the prior art, the first embodiment of the medical treatment support system includes the input/display device 2 in the form of an integrated system in place of the input device and the display of the prior art. Thereby, an advantageous user interface is provided in a physical operation for the medical reports on sheets of paper by the system in accordance with the present invention.

The storage 1 stores storage data which is updated by a storage data update controller 3b of the controller 3.

Figure 2:
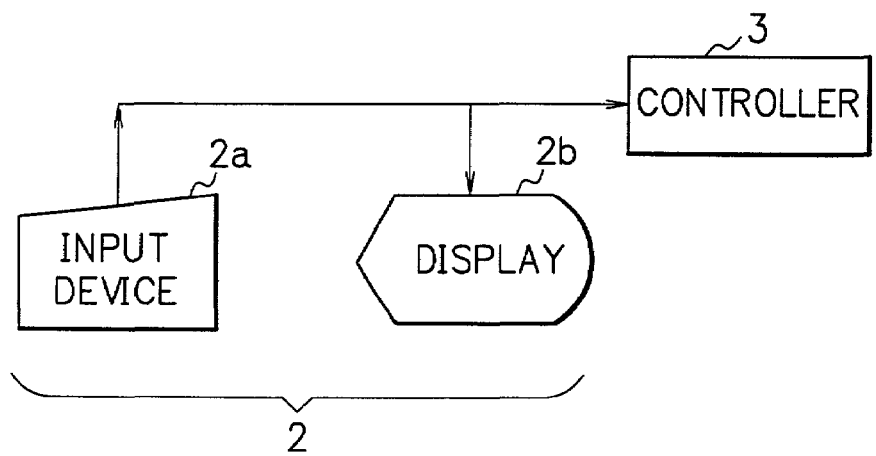
FIG. 2 is a block diagram showing structure of an input/display device used in an embodiment of the present invention.

The input/display device 2 is a liquid-crystal pen-tablet unit or the like in which an input device 2a and a display 2b are integrally combined with each other as shown in FIG. 2. The input device 2a is a pen-tablet pointer constructed in the form of a pen. The operator can input characters and indications of operation by directly touching a surface of the thin type display 2b such as a liquid-crystal display or PDP (plasma display panel) using the input device 2a.

The controller 3 includes a display data generation controller 3a and a storage data update controller 3b. The controller 3 further includes a print data generation controller 3c preferably.

The communication device 4 serves as a communication interface to control communication of data with other systems or other communication devices.

The printer 5 prints, on a sheet(s) of paper, print data generated by the print data generation controller 3c of the controller 3.

Figure 3:
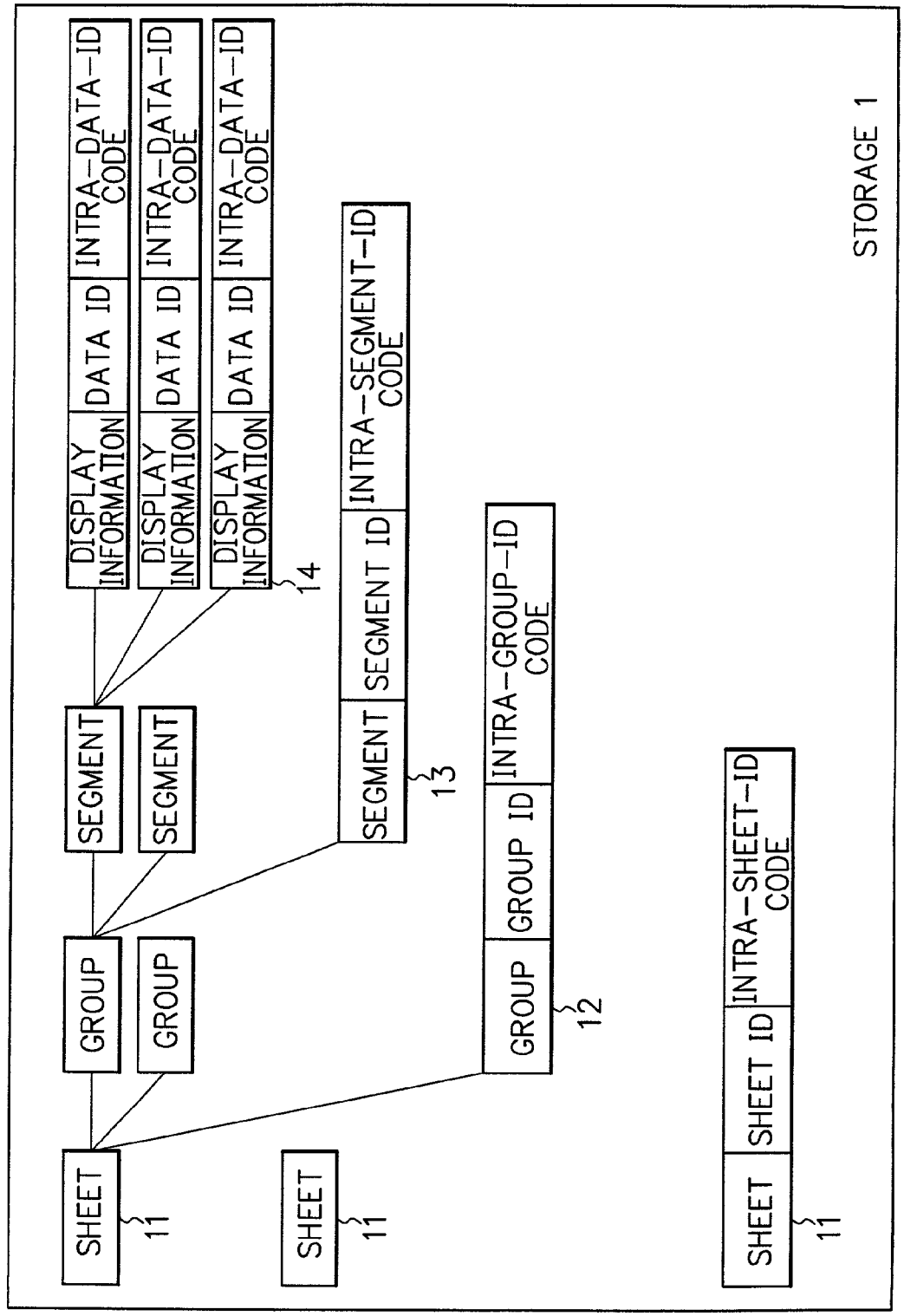
FIG. 3 is a diagram showing a data management state of a storage in an embodiment of the present invention.

FIG. 3 shows a data management state of a storage used in the first embodiment in accordance with the present invention. The storage of FIG. 3 includes storage units hierarchically ordered.

The storage units control a sheet 11, a group 12, and a segment 13, respectively. The sheet 11, the group 12, and the segment 13 are structurally controlled and stored and can be therefore copied and transferred data, files, applications or the like.

Each segment is controlled by a storage unit and controls each element 14 in a segment corresponding to the storage unit. Each element 14 is used to search an intra-data-identifier code according to display information (input contents) and a data identifier.

Figure 4:
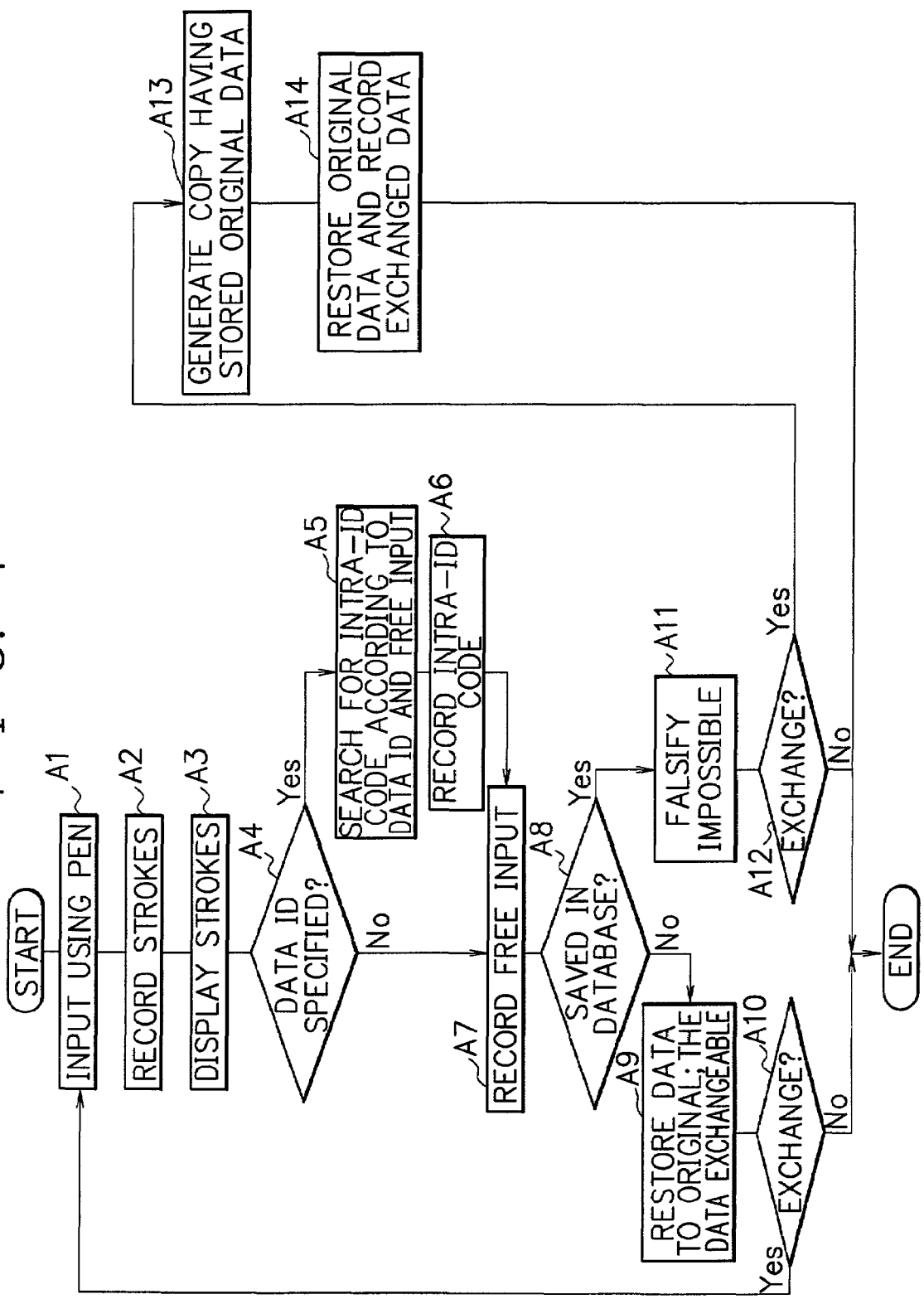
FIG. 4 is a flowchart showing an operational example of the first embodiment of a medical treatment support system in accordance with the present invention.

FIG. 4 shows an example of operation of the first embodiment of the medical treatment support system in accordance with the present invention in a flowchart. First, the operator starts a pen input operation using the input/display device 2 (step A1). The display data generation controller 3a then stores input strokes in a vector representation (step A2) and displays the strokes (step A3). The storage data update controller 3b makes a check to determine whether or not a data identifier has been specified in the input stroke information (step A4).

If it is found in step A4 that the data identifier has been specified (yes in step A4), the controller 3b makes a search for an intra-identifier code according to the data identifier and free input (step A5) and records the intra-identifier code (step A6).

If it is found in step A4 that the data identifier has not been specified (no in step A4), the controller 3b records free input (step A7).

Finally, the storage data update controller 3b controls a function to restore an operation error. Specifically, the controller 3b determines whether or not the recorded contents have been saved in a database (storage; step A8).

The medical treatment support system in the first embodiment of the present invention includes two kinds of databases for respective purposes. The first database is classified in every patient data or files. Another database is stored data in predetermined time. For example, the first database is used to control history of handwritten strokes. All strokes on the screen at any point of time and additional information such as a point of time and a color are automatically recorded without any explicit saving operation. The second database is, for example, used to save data in an integrated manner. Data is recorded in the database by an explicit saving operation.

The data saving in the database in step A8 is conducted to save information regarding medical treatment in the form of data in an integrated manner. The explicit saving operation includes the depression of a Lock button 200 and an operation to explicitly close a medical report (information of medical treatment for the pertinent patient) after the medical treatment. As a result, the input data of the pertinent group is saved and/or data inputted during the medical treatment of the patient is saved. For a group displayed according to the data saved in the database, an unchangeable state is explicitly indicated. The explicit indication of the unchangeable state is indicated, for example, by a tag representing the Lock button 200 in a depressed state at a lower-right corner or an upper-right corner of the group, by a shaded area, or by a color.

In step A8, if the data is not saved (not stored) in the database, it is possible to conduct a restoring operation (step A9). Thereafter, presence or absence of a change is determined (step A10). If the change is to be executed, the processing returns again to step A1 for the pen-input operation.

On the other hand, in step A8, if the data is saved (stored) in the database, the falsification becomes impossible (step A11). For a change of the contents which cannot be falsified, presence or absence of a change is determined (step A12). A copy having stored the original data is generated (step A13) and then the changed data is recorded (step A14).

In this operation, the original data is not directly changed, but information is added to the generated copy. The resultant data and the original data are saved in a mutually independent way. The additional information includes information to identify a change operator, information to indicate the original data, and information of input strokes for the change operation. This resultantly prevents falsification of the information regarding the medical treatment, and there are provided a function to change the original data and a function to restore the original data regardless of presence or absence of the database.

Figure 5:
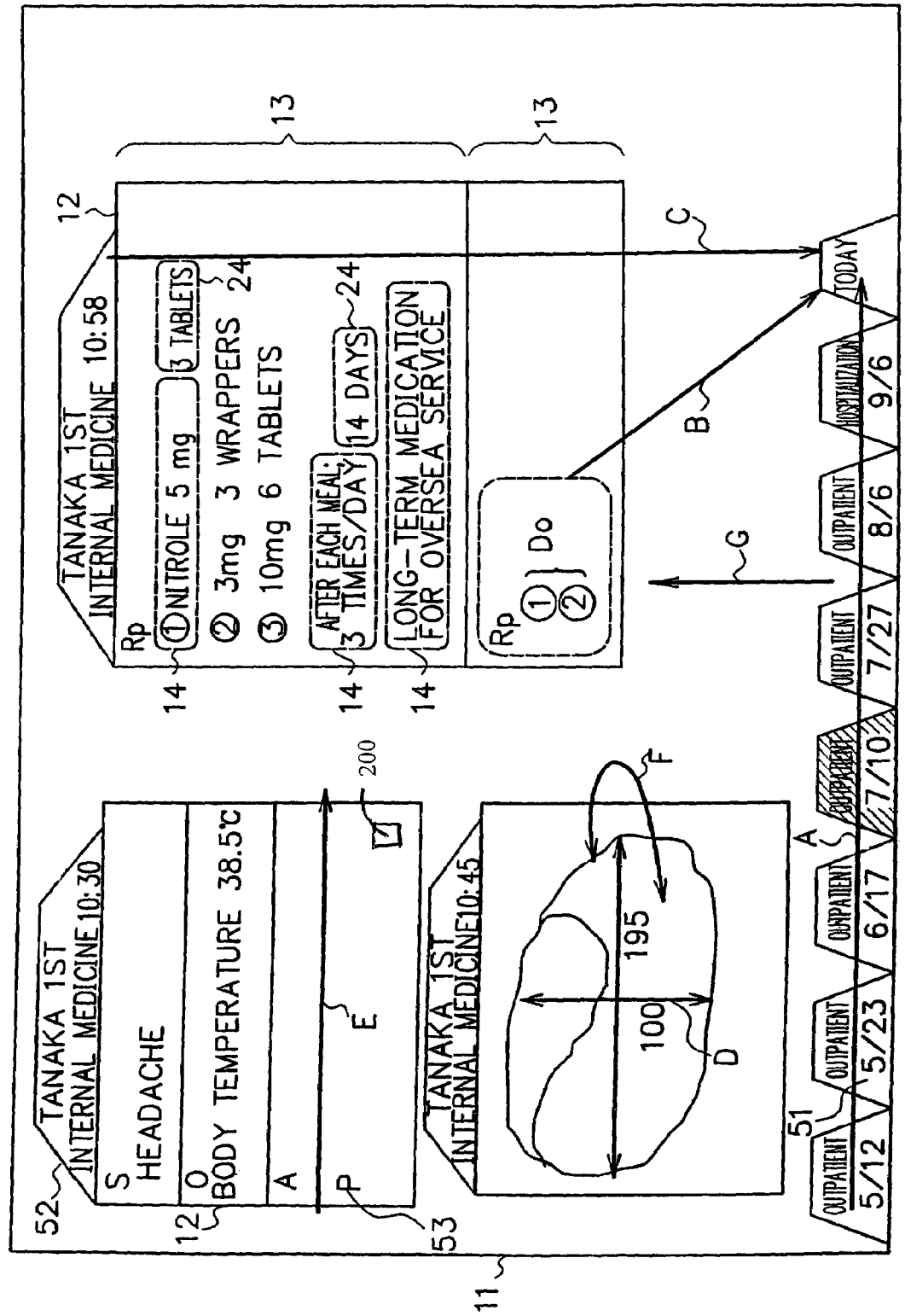
FIG. 5 is a diagram showing a first display example of the input/display device used in the embodiment of the present invention.

FIG. 5 shows a first display example of the input/display device used in the first embodiment in accordance with the present invention. In the configuration of FIG. 5, when a pen-input operation is started, a sheet 11, a group 12, and a segment 13 are automatically generated. Tags are automatically added to labels 51 to 53. The system has a copy function and a move (transfer) or shift function.

The sheet 11, the group 12, the segment 13, and an element 14 respectively correspond to their respective storage units. Input strokes in vector notation and identifier information are stored and hence a desired input operation can be conducted by hand.

In FIG. 5, operations A to G represent are useful to easily handle respective data items on the sheet 11. Operations B and C are functions to facilitate "copy" and "shift". However, the shift is used only as reference. Aim of present invention is to defend not to change data inequality. Operation D is a ruler function for easy measurement. Operation E is a function to easily conduct segment division only by drawing a horizontal line. Operation F is a function to rotate an image displayed on the screen. Operation G is a function to browse data items stored in conjunction with sheet labels displayed in a bottom section of the screen.

When a pen-input operation starts, a sheet 11 is automatically generated and then a sheet label 51 is automatically added thereto. The sheet label 51 includes at least a date. For an outpatient, the sheets are generated as many as the outpatient visits the hospital or clinic. The label is automatically added to each sheet. For an inpatient, a desired number of sheets are generated while the inpatient is staying in the hospital. The label is automatically added to each sheet. On each sheet thus generated for each medical treatment as above, the contents of medical treatment are described. That is, the sheet has a function similar to a sheet of paper and hence can be treated in almost the same manner as for the ordinary sheet of paper. When changing the sheet, the operator uses operation A to successively refer to information in the past. That is, the operator does not select an item such as a date from a menu at a fixed position on the screen. Operation A is specifically conducted as follows. The operator pushes the pen onto a sheet label and slides the pen to successively display the past medical reports as if the operator turns pages of a book.

Additionally, when a pen-input operation is conducted on each sheet, a group 12 is automatically generated. A group label 52 is automatically added thereto as shown in FIG. 5. The group label 52 constitutes in addition to at least an operation time. Information of respective groups is divided into several segments in be controlled by a segment 13 which is part of a storage unit. When operation E for the segment division is activated, a segment is automatically divided by drawing a horizontal line as shown in FIG. 5, and a segment label 53 is automatically attached (added). The contents of the segment label 53 are determined by a group identifier of a group specified in advance.

For example, a segment label 53 to be automatically added by operation E is "P (Pharmaceuticals)". When a pen-input operation is started and a group 12 is generated, group identification is automatically conducted for input of "S, O, A, P". In a group of identification of the "S, O, A, P" input, label "S", "O", "A", and "P" are automatically attached beginning at a highest row. Label "P" is automatically displayed for a fourth segment.

In this regard, the "S, O, A, P" input collectively represents items of a general medical report: S for "Subject" (contents of primary complaints and inquiries: diagnosis or ask a patient about his/her condition), O for "Object" (medical finding), A for "Assessment (medical assessment)", and P for "Plan" (medical treatment plan).

In the group 12 shown in the right section of FIG. 5, the group identifier is "medicine indication input (inputting direct to pharmaceuticals)", a segment label of "Rp (Recipe or Recipe of pharmaceuticals)" is automatically generated. The group identifier specification is selected from a pop-up menu.

Using operation B, the operator can drag a segment to drop the segment at a sheet label in which a date or the like is displayed. Resultantly, a copy of the segment can be added to a medical report of the date (see drag and drop for "Windows". . . . The present invention may be an another OS having a same function about "drag and drop".).

Operation C is used to copy a group. For example, when the contents of a medical report of an outpatient in the hospital are the same as those of the last medical report, a copy function of a sheet, a segment, or a group can be used as "previous-case DO" to generate the same prescription as that of the previous medical treatment. For information copied or moved for the operation to refer thereto, the operator may use a function to clearly indicate, for example, by a color that the information is in an unchangeable state.

As shown in FIG. 5, the elements 14 in the segment 13 are used to increase the keyword retrieval speed. For the purpose, each element 14 has a function in which contents inputted by the pen are coded into a code to keep the code therein. For example, when a medical treatment support is conducted using results of past data analyses, it is desirable that the contents of input items are stored in the coded form.

The contents inputted by the pen are graphically recorded in a storage in the form of an array of values of coordinates. Processing to convert the contents of the array through character recognition into text information including an array of character codes is referred to as "coding".

The segment 13 includes a plurality of elements 14 as shown in FIG. 5. For example, when the group identifier is "medicine indication input", a data identifier of "medicine", a data identifier of "usage", and a data identifier of "comment" exist for each element 14.

Specifically, in a retrieval of a medicine named "A-I-U", the operator inputs "A" by the pen and then a character recognition step is conducted. Next, the system displays a list of medicines which has a data identifier of "medicine" and of which the first letter or character is "A". When the operator selects a desired medicine from the list, a coding step is conducted. This function co-exists the input of the prior art, for example, an input from a software keyboard.

Operation D serves as a ruler function to measure length on the screen. In a concrete operation, when the operator draws a line on the screen using the drag function, the length of the line is displayed. For example, in a situation in which an image report such as an x-ray photo or an x-ray photo scanned is being displayed on the sheet, the operator selects the ruler function from, for example, the pop-up menu and measures the length on the screen.

In operation D, by recognizing measured values 100 and 195 in the unit of pixels, a ratio (magnification or scaling factor) can be displayed as shown in FIG. 5. If a scale exists in the system, the values actually measured can be automatically calculated. Additionally, using operation F to rotate the information of a two-dimensional or three dimensional image displayed on the screen, the operator can easily measure the image in various directions.

Figure 6:
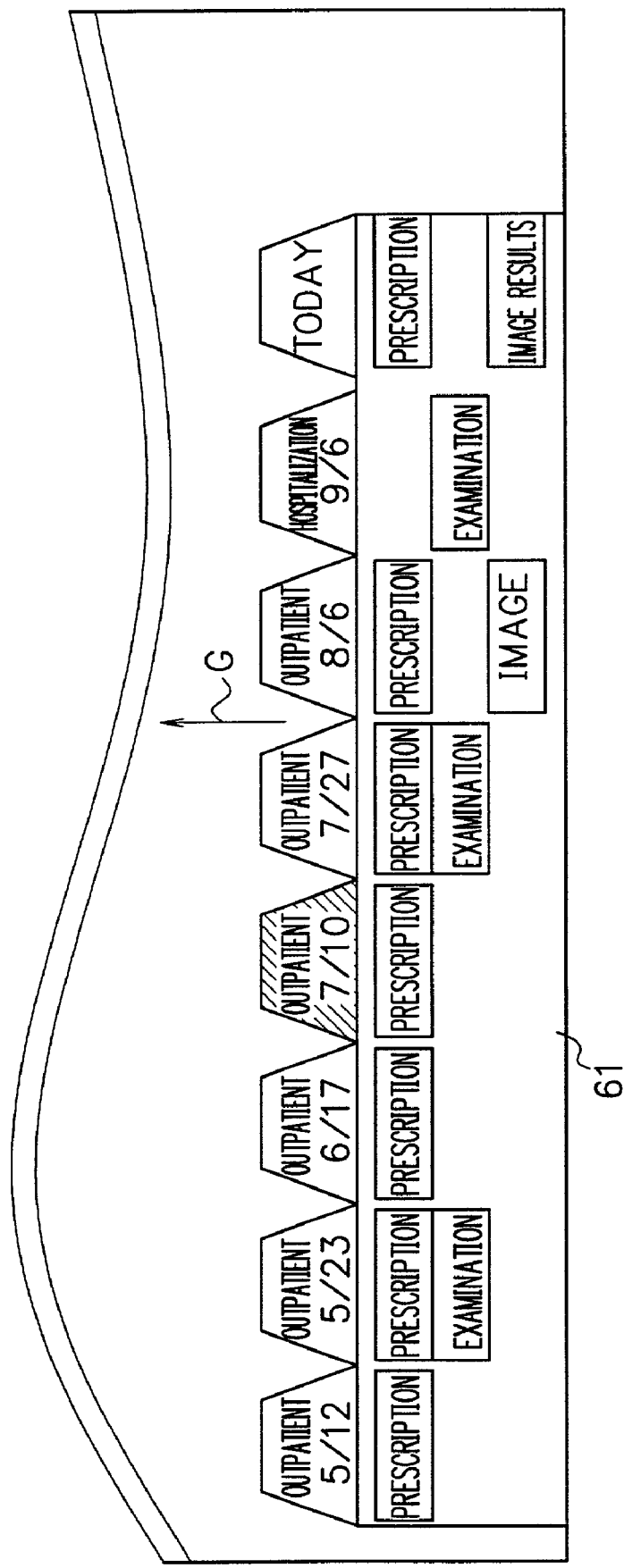
FIG. 6 is a diagram showing a second display example of the input/display device used in the embodiment of the present invention.

Operation G is an operation in which the operator raises the overall image of the tags (sheet labels) displayed on the screen to browse data associated with the sheet labels (a function which is transferred an another page or segment). FIG. 6 shows a second display example displayed by operation G in the input/display device.

In operation G, when a drag operation is conducted at an arbitrary position between the sheet labels in a direction indicated by an arrow mark, the all sheet labels are dragged in the direction. Below each sheet label, group identifier information 61 associated with the sheet label is displayed. In the group identifier information 61, group identifiers of the same type are displayed in one row. Therefore, the operator can be easily and visually recognize the same kind of information. For example, to refer to arbitrary data in the group identifier information 61, when the operator slightly depresses a label of the pertinent data by the pen or drags the label by the pen to a position at which the data is displayed, it is possible to refer to the data. At this point of time, the data is assumed as data to be referred to, and hence is displayed in a state other than the state of the other groups. For example, the data is indicated by a mark or is colored to indicate that the data is unchangeable.

FIG. 7 shows a third display example of the input/display device used in the present invention. In FIG. 7, operation H is a function to display data for higher visual recognition. In this way, the advantages of the electronic processing system and the handwriting system using sheets of paper can be obtained in accordance with the present invention.

In operation H, data is displayed in a magnified, minimized, or depressed image using a shift or move operation. Specifically, the operator drags a left-side group 12*a* toward a group 12*b*. Immediately before the group 12*a* overlaps with the group 12*b* in the displayed image, the group 12*b* is moved in the direction of operation H. When the group 12*b* moves to a point just before a frame of the sheet 11, the system starts minimizing only the group 12*b*. In this situation, the group 12*a* is not minimized. When the group 12*a* is further moved in the direction of operation H, the group 12*a* is displayed in a depressed state.

Conversely, when operation H is conducted in the reverse direction, the system starts magnifying the minimized group 12*b* to the original display size. When the operator drags only the group 12*a* to an end position of the sheet 11, the system starts the minimization of the group 12*a* immediately before the group 12*a* overlaps with the sheet 11. As above, the group 12 and segment 13 on the sheet 11 have the function for visual recognition, namely, the magnification, minimization, and depression of the image.

Operation I is used to adjust width of each segment resultant from the segment division. As in the case of operation H, when a particular segment is moved, the magnification, minimization, or depression of the image is conducted immediately before the segment overlaps with another segment or the display frame on the screen.

Figure 8:
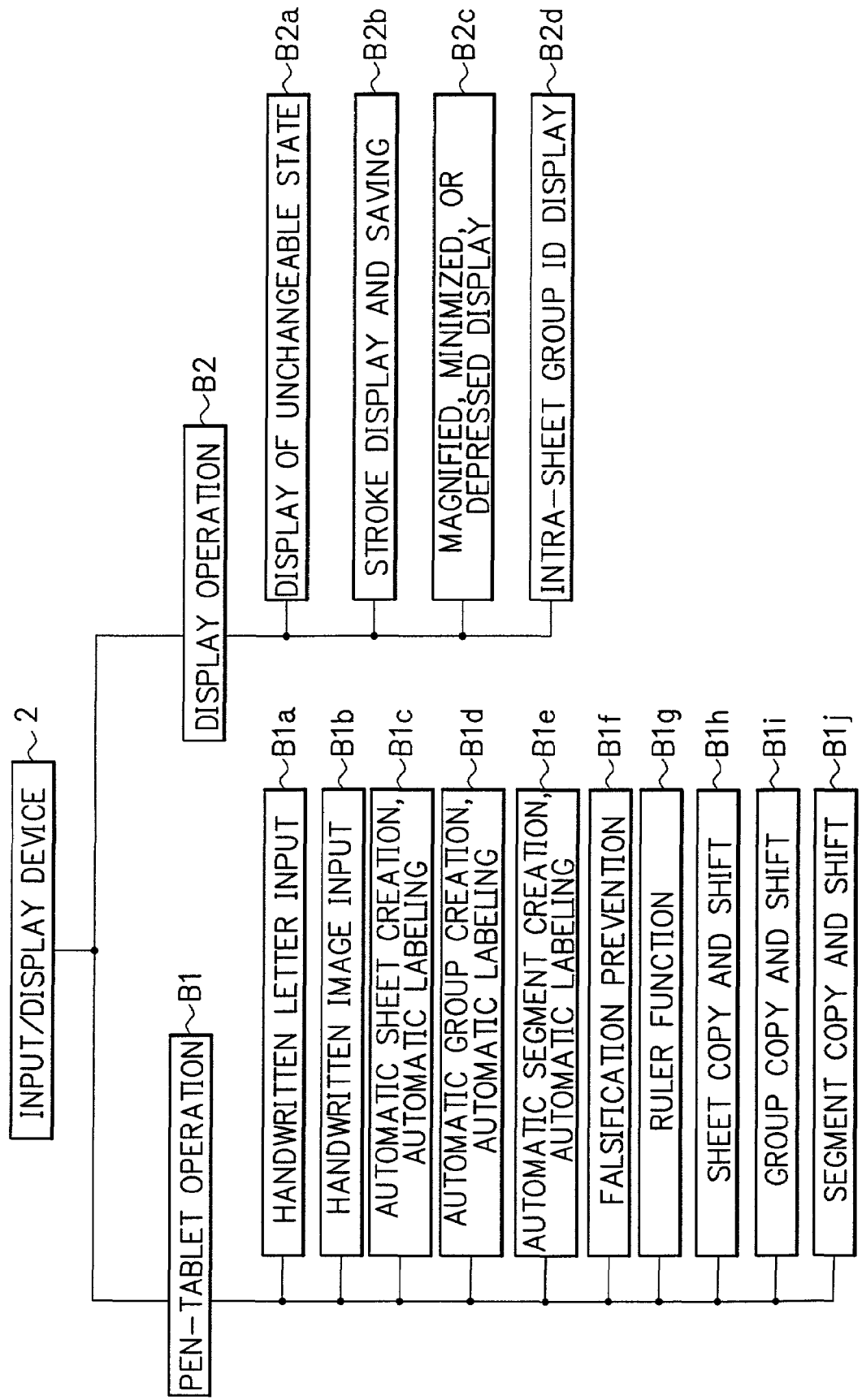
FIG. 8 is a diagram showing operation of the input/display device used in the embodiment in accordance with the present invention.

FIG. 8 schematically shows operation of the input/display device used in the present invention. The input/display device 2 conducts two main operations including a pen-tablet operation B1 and a display operation B2.

As shown in FIG. 8, pen-tablet operation B1 is used to execute processing such as "handwritten letter input B1*a*", "handwritten image input B1*b*", "automatic sheet creation, automatic labeling B1*c*", "automatic group creation, automatic labeling B1*d*", "automatic segment creation, automatic labeling B1*e*", "falsification prevention B1*f*", "ruler function B1*g*", "sheet copy and shift B1*h*", "group copy and shift B1*i*", and "segment copy and shift B1*j*".

Display operation B2 is used to execute processing such as "display of unchangeable state B2*a*", "stroke display and saving B2*b*", "magnified, minimized, or depressed display B2*c*", and "intra-sheet group ID display B2*d*". The display operation B2 can be conducted for each group and for each segment.

Second Embodiment

Next, description will be given of a second embodiment in accordance with the present invention in which a plurality of operators can conduct a plurality of pen-input operations.

Figure 9:
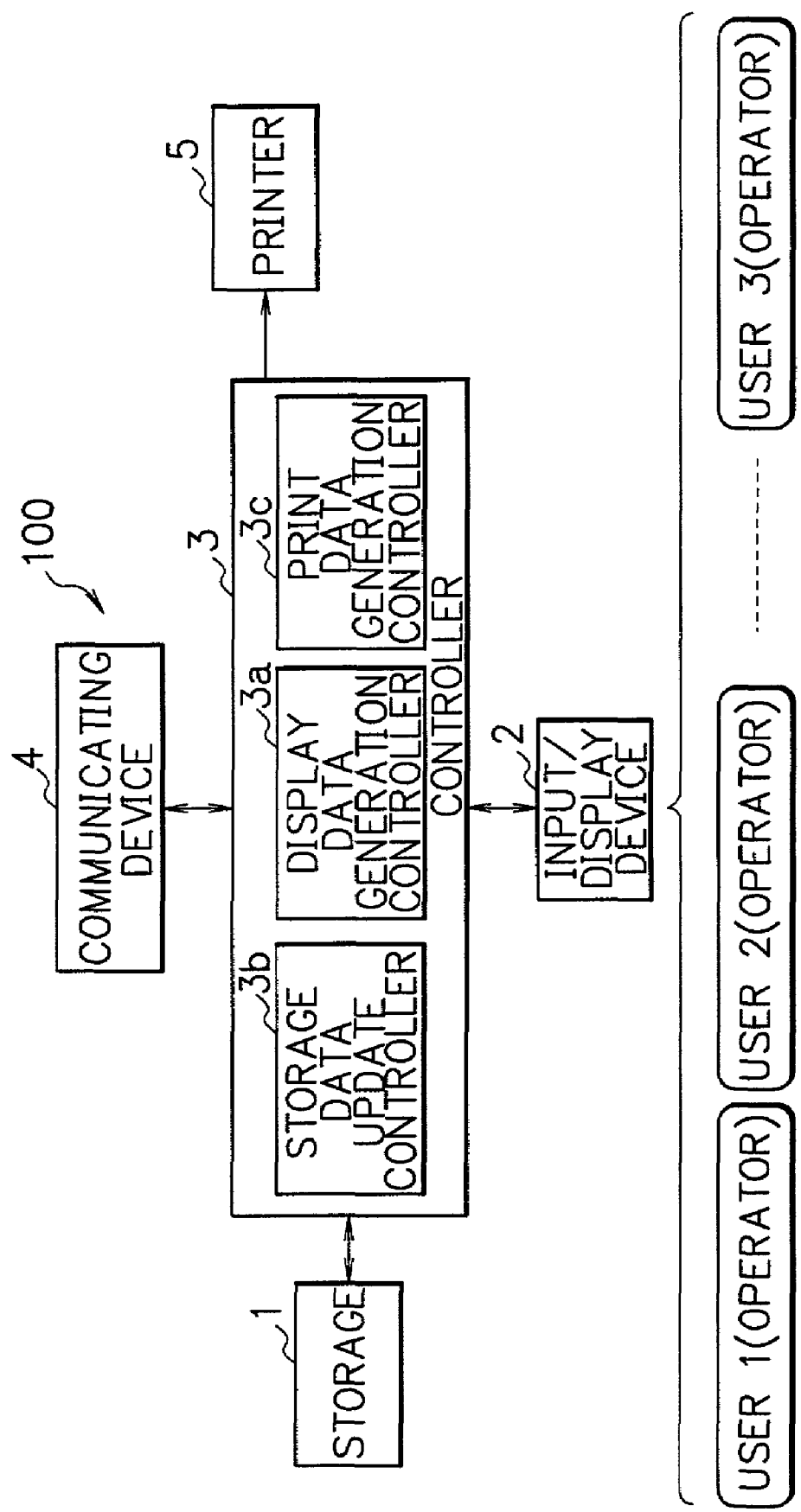
FIG. 9 is a block diagram showing an outline of the configuration of a second embodiment of a medical treatment support system in accordance with the present invention.

FIG. 9 shows an outline of the configuration of a second embodiment of a medical treatment support system in accordance with the present invention is a block diagram. The second embodiment differs from the first embodiment in that a plurality of operators, namely, users 1 to n operate the single-unit input/display device 2.

Figure 10:
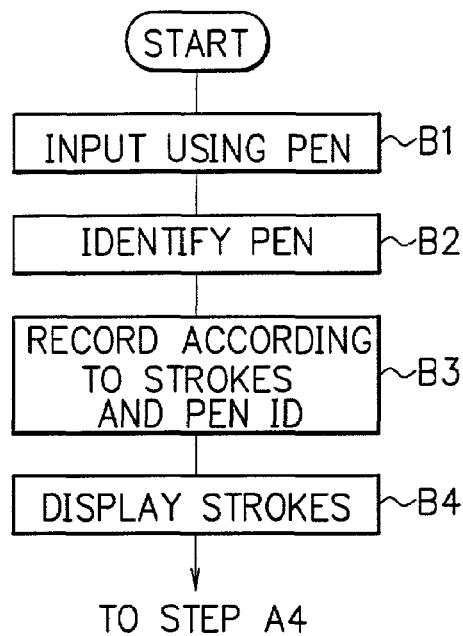
FIG. 10 is a flowchart showing an example of operation of the second embodiment of a medical treatment support system in accordance with the present invention.

FIG. 10 shows a flowchart of an example of operation of the second embodiment of the medical treatment support system in accordance with the present invention. In the flowchart, steps A1 to A3 of FIG. 4 are replaced by steps B1 to B4. First, the operator starts pen-input operation from the input/display device 2 (step B1). In response thereto, the display data controller 3*a* identifies the pen to identify the operator (step B2). The controller 3*a* records input strokes and a pen identifier in a vector representation (step B3) and then displays the strokes (step B4). Subsequent steps are almost the same as step A4 and subsequent steps of FIG. 6. However, the processing of the second embodiment has a different point that information of a pen identifier is additionally employed to identify the operator when the input strokes are stored.

Subsequently, description will be given of a specific example of the second embodiment of the medical treatment support system in accordance with the present invention. As can be seen from FIG. 10, the users or operators respectively have own particular pens or badges to conduct pen-input operations for one sheet of the input/display device 2. Each particular badge is part of an input device including an automatic pen identifying function. Since a pen identifier to identify its operator is added to each record of input strokes, the input strokes can be managed for each operator. Therefore, when a medical treatment team including persons of various occupations and jobs conducts a discussion for an appropriate medical treatment, it is possible that many operators share the input/display device 2. In the present invention, the above-mentioned particular badges or pens used only for checking who inputs newly writing data. Therefore, in the badge(s) there is some recognizing, matching or authentication data at least one, for example, an optical inputting data containing pixel(s). From the badge, the system used in the present invention reads the data contained the badge directly or through a reader (an optical reader) or the like. Or the badge may emit optical signals or radio frequency signals. The system identifies who inputs data (writing data), classifies inputting data by identified a named person and stores as the named person's file(s).

If a person as the named person (an identified person) inputs data, an inputting person and the identified person are same or different by recognizable the input handwriting data.

Furthermore, the present invention may input data and store the data when

Third Embodiment

Figure 11:
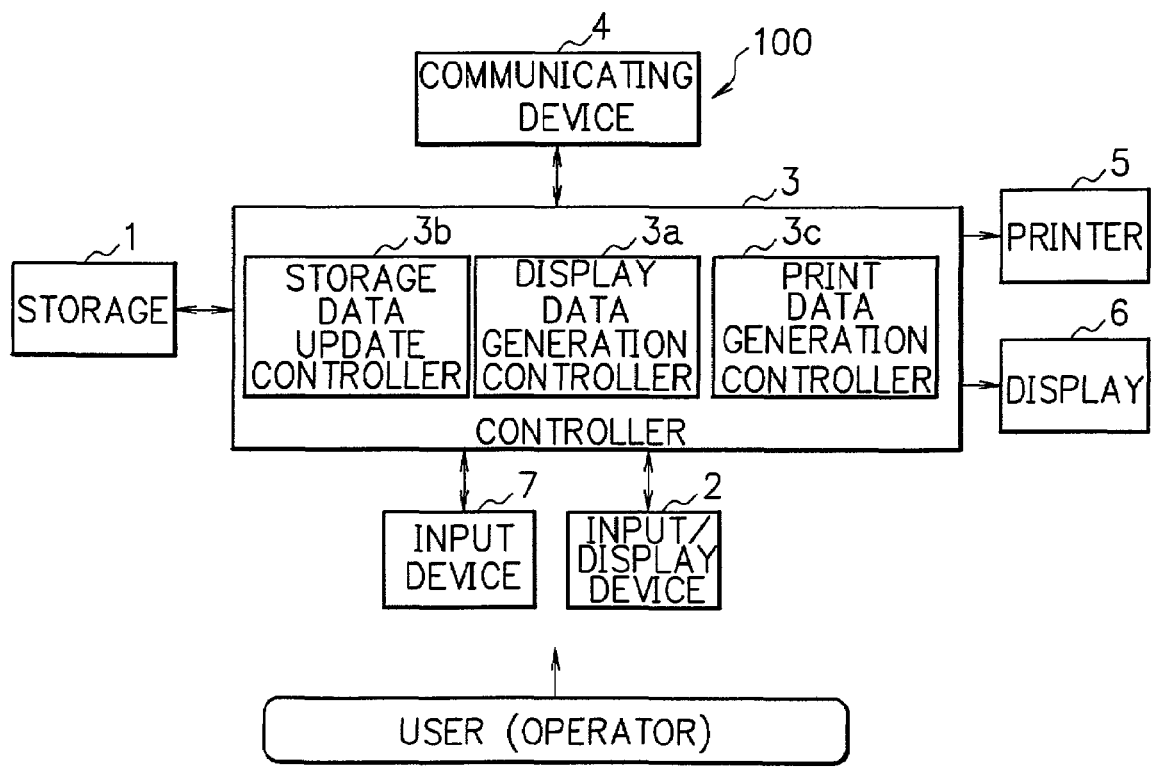
FIG. 11 is a block diagram showing an outline of the configuration of a third embodiment of a medical treatment support system in accordance with the present invention.

FIG. 11 shows an outline of the configuration of a third embodiment of a medical treatment support system in accordance with the present invention in a block diagram. The medical treatment system 100 of FIG. 11 includes a storage 1, an input/display device 2, a controller 3, a communication device 4, a printer 5, a display, and an input device 7.

The display 6 may be a display of the prior art or may be a liquid-crystal display in accordance with the present invention. In addition, the number of the displays 6 is not limited to one, that is, a plurality of displays 6 may be simultaneously connected to the system. The input device 7 includes a keyboard and a ten-key pad of the prior art. The display 6 and the input device 7 can operate in the same system.

The third embodiment of the present invention has a function to reflect in the display 6 necessary items of the contents of data processed by the input/display device 2. The third embodiment differs from the preceding embodiments in that the contents which are inputted from the input device 7 and which are then confirmed by the display 6 are reflected in the input/display device 2. Moreover, the third embodiment includes a plurality of input/display devices 2 and data is mutually reflected in the input/display devices.

The display data generation controller 3a controls data to be displayed on the input/display device 2 and the display 6. The system may be used, for example, as follows. According to respective processing of a multi-display control program to display data on many displays and inputs from users to display data in desired formats, the system displays image data on the input/display device 2 on which various items are written by a cordless pen, and electronic medical report information is displayed on the display 6 such that additional items are written in the information.

Next, description will be given in detail of a third embodiment of the medical treatment system in accordance with the present invention. First, description will be given of an example in which the system is used for informed consent of a patient. On a medical report screen in which a medical treatment and the like are described, the operator specifies information necessary for explanation and then displays an explanation screen. When the explanation screen belongs to a single-unit input/output device, the explanation is conducted by directly describing information in the display screen. For detailed explanation, it is possible to manually input on the data or to draw a picture beside the data. The screen used for the explanation can be displayed on the medical report screen in which a medical treatment and the like are described so that these screens are saved at a time. The saved information can be used for subsequent explanation.

Subsequently, description will be given of an example which uses an application prepared for use with the display 6 and the input device 7 of the prior art. While keeping the medical report information displayed on the input/display device 2, the user operates the display 6 or the input device 7. When the operation is completed, necessary items of the contents of the input are automatically reflected in the input/display device 2 to display the medical report information.

Figure 12:
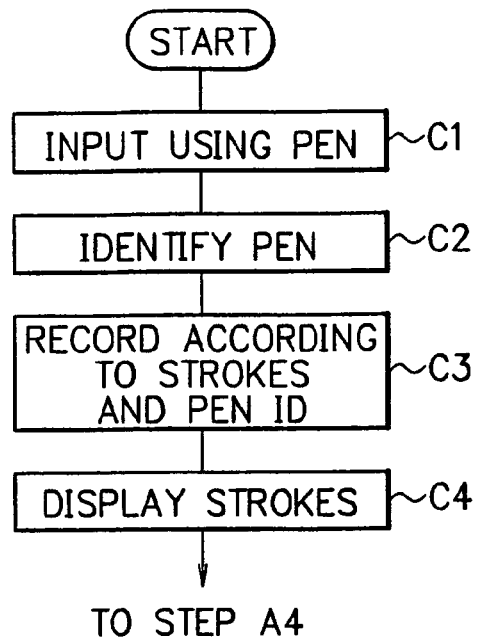
FIG. 12 is a flowchart showing an example of operation of the third embodiment of a medical treatment support system in accordance with the present invention.
Figure 13:
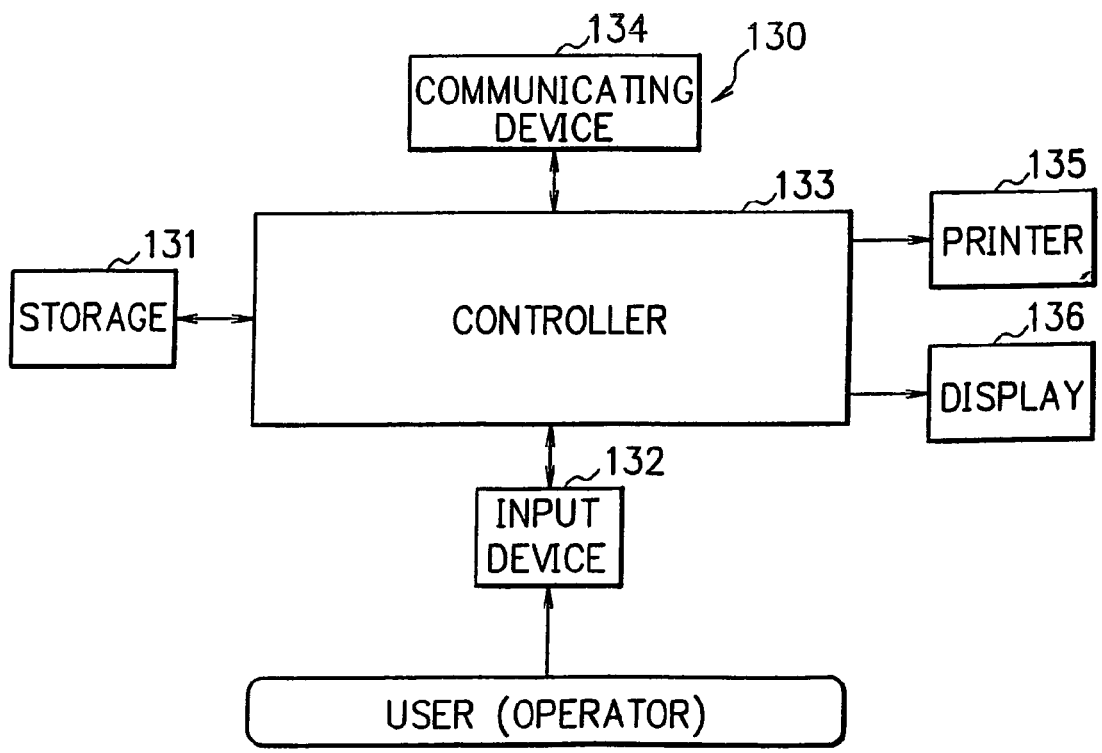
FIG. 13 is a block diagram showing an outline of the configuration of a medical treatment support system in the prior art.

FIG. 12 partially shows in a flowchart an example of operation of the third embodiment of the medical treatment support system in accordance with the present invention. FIG. 12 corresponds to steps A1 to A3 of FIG. 6. First, the operator starts pen-input operation from the input/display device (step C1). In response thereto, the display data controller 3a identifies the screens (step C2). The controller 3a records input strokes and screen identifiers in a vector representation (step C3) and then displays the strokes (step C4). Subsequent steps are almost the same as step A4 and subsequent steps of FIG. 6. However, the processing of the third embodiment has a different point that information of a screen identifier is additionally employed to identify the screen when the input strokes are stored.

The foregoing embodiments are those suitable for the present invention and can be changed or modified in various ways without departing from the scope and spirit of the present invention. For example, a client-server system can be configured in which a server includes a storage and a controller and a plurality of input/display devices each including a communicating function to access the server.

The processing program of the embodiments in accordance with the present invention is stored on a storage medium disposed in the controller. The recording medium may be, for example, a magnetic disk, a compact-disk read-only memory (CD-ROM), and/or a semiconductor memory. The controller activates the respective devices to execute processing according to the processing program recorded on the recording medium.

As can be seen from the description above, according to a medical treatment support system, a display method for the same, and a recording medium having stored a program of the same in accordance with the present invention, new functions added to the integrated input/output pen-tablet can be intuitively operated by an operator who has not versed in the operation of the functions. Therefore, the load on the complex input operation which interrupts thinking of the operator and which hinders the medical diagnosis can be mitigated.

Furthermore, according to a medical treatment support system, a display method for the same, and a recording medium having stored a program of the same in accordance with the present invention, data can be freely copied or moved for each sheet, each group, and each segment. Consequently, information collected in the past can be easily referred to and can be used for another purpose in the medical treatment.

Additionally, according to a medical treatment support system, a display method for the same, and a recording medium having stored a program of the same in accordance with the present invention, it is possible to instantaneously browse a large amount of information gathered in the past. Therefore, in the medical treatment, a large amount of medical reports in the past can be sequentially displayed to easily detect desired information.

According to a medical treatment support system, a display method for the same, and a recording medium having stored a program of the same in accordance with the present invention, input strokes are stored in the vector representation, not in the bit-map representation. In consequence, the memory amount used to store the input strokes is reduced, and data is displayed according to optimized information. Therefore, screen images can be displayed at a high speed in the medical treatment.

Moreover, according to a medical treatment support system, a display method for the same, and a recording medium having stored a program of the same in accordance with the present invention, there is provided a function to convert a necessary portion of handwritten characters manually inputted into codes. Data can be stored in the form of codes, and hence the key-word retrieval can be conducted at a high speed, and data collected in the past can be easily retrieved. Consequently, in the medical treatment support system, the past information can be readily used in the medical treatment.

According to a medical treatment support system, a display method for the same, and a recording medium having stored a program of the same in accordance with the present invention, an operation to measure distance can be conducted by a simple operation in which the operator draws a line on the screen. Therefore, in the medical treatment support system, image reports can be used for the diagnosis in the medical treatment.

Moreover, according to a medical treatment support system, a display method for the same, and a recording medium having stored a program of the same in accordance with the present invention, an image which is partially concealed or which can be displayed using a screen-change operation because of the limitation of the screen display size can be minimized. Therefore, the image is kept remained and can be visually recognized as a minimized image on the screen. The operation can be accordingly conducted while continuously and visually recognizing the displayed data. Consequently, the thinking of the operator is not interrupted and hence the operator can concentrate on the medical treatment and the diagnosis.

According to a medical treatment support system, a display method for the same, and a recording medium having stored a program of the same in accordance with the present invention, input strokes are stored. Therefore, when an operation error takes place, the error can be canceled or data associated with the error can be restored for the storage thereof. To change information registered to the database, the original data is not directly changed. While explicitly showing the original data, input strokes are saved as history of the correction. Therefore, the falsification of the data can be prevented.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention. In this specification, terminology about function of menu or application or the like, is used about some OS. However, the present invention is not limited to the some OS specifically. The invention may use any OS which has a same function of described above.

What is claimed is:

1. An application method for supporting a medical treatment system, the system comprising an input/display device, a storage, and a controller, said input/display device including input means and display means, said storage comprising a first database that stores a history of input stroke information automatically and a second database that stores explicit saving operations initiated by a user, said input stroke information comprising handwritten strokes, said controller comprising a display data generation controller, a storage data update controller, and a print data generation controller, the method comprising:

the input/display device receiving said input stroke information by handwriting, said handwriting comprising directly touching a surface of said display means with said input means, said input/display device comprising a pen-tablet unit, said pen-tablet unit comprising said input means and said display means integrally combined, said input means comprising a pen-tablet pointer having a pen shape, said display means being one of a liquid-crystal display and a plasma display panel;

first storing said input stroke information in a vector representation in said storage using said display data generation controller;

displaying said input stroke information on said display using said display data generation controller;

first determining whether a data identifier has been received in said input stroke information, said storage data update controller performing said first determining such that if said data identifier is received in said input stroke information, then said first determining comprises:

searching for an intra-identifier code according to said data identifier and free input, said storage data update controller performing said searching; and data-identifier recording said intra-identifier code, said storage data update controller performing said data-identifier recording;

free-input recording said free input, said storage data update controller performing said free-input recording;

enabling said user to save said intra-identifier code and said free input in said storage substantially all as medical data;

the input means moving in a sliding manner on a sheet label displayed at a particular position on a screen by the display means;

the input/display device reading, when the input means moves onto said sheet label, data stored in said storage in relation to said sheet label from said storage, and displaying the data by conducting a change-over operation for said sheet label;

second determining whether said intra-identifier code and said free input are saved in said storage, said second determining using said storage data update controller to control said second determining such that, if said intra-identifier code and said free input are not saved in said storage, a restoring operation is conducted, then said restoring operation comprises:

third determining whether a first change in said storage has occurred;

returning to said input/display device receiving said input stroke information to repeat said application method up to said second determining if said first change in said storage has occurred; and first ending said application method if said first change in said storage has not occurred;

declaring a falsification of said intra-identifier code and said free input to be impossible if said restoring operation is not conducted;

fourth determining whether a second change in said storage has occurred;

second ending said application method if said second change in said storage has not occurred; and if said second change in said storage has occurred, generating a copy of said storage without said intra-identifier code and said free input storage, recording said second change in said storage, and ending said application method.

2. The application method for supporting a medical treatment system in accordance with claim 1, wherein, when segments of an input field are displayed, segment labels are assigned to the segments according to a plurality of data identifiers previously specified to the respective segments.

3. The application method for supporting a medical treatment system in accordance with claim 2, further comprising:

conducting character recognition processing of said receiving of said input stroke information to determine if a character is received in said input stroke information, wherein said input/display device conducts said character recognition processing for said input stroke information inputted from said input means and comprising an array of values of coordinates, converts by said character recognition processing said input stroke information into text data including an array of character codes, and displays the text data.

4. The application method for supporting a medical treatment system claimed in claim 1, wherein, in the storage, the medical data are stored after one of a depression of a lock button and an operation to explicitly close a medical report.

5. The application method for supporting a medical treatment system in accordance with claim 4, further comprising:
conducting character recognition processing of said receiving of said input stroke information to determine if a character is received in said input stroke information,
wherein said input/display device conducts said character recognition processing for said input stroke information inputted from said input means and comprising an array of values of coordinates, converts by said character recognition processing said input stroke information into text data including an array of character codes, and displays the text data.

6. The application method for supporting a medical treatment system in accordance with claim 4, wherein, when segments of an input field are displayed, segment labels are assigned to the segments according to a plurality of data identifiers previously specified to the respective segments.

7. The application method for supporting a medical treatment system in accordance with claim 6, further comprising:
conducting character recognition processing of said receiving of said input stroke information to determine if a character is received in said input stroke information,
wherein said input/display device conducts said character recognition processing for said input stroke information inputted from said input means and comprising an array of values of coordinates, converts by said character recognition processing said input stroke information into text data including an array of character codes, and displays the text data.

8. The application method for supporting a medical treatment system in accordance with claim 1, further comprising:
conducting character recognition processing of said receiving of said input stroke information to determine if a character is received in said input stroke information,
wherein said input/display device conducts said character recognition processing for said input stroke information inputted from said input means and comprising an array of values of coordinates, converts by said character recognition processing said input stroke information into text data including an array of character codes, and displays the text data.

9. The application method for supporting a medical treatment system in accordance with claim 8, further comprising:
the input means dragging a particular input field selected from a plurality of input fields displayed at particular positions on a screen by said display means and dropping the particular input field onto said sheet label;
said storage storing data of said particular input field with a relationship established to said sheet label;
the input means dragging a sheet label displayed at positions on a screen by the display means and moving the sheet label upward;
the input/display device reading data stored in the storage in relation to the sheet label from the storage and displaying the data below the sheet label based on the type of stored data;
the input means dragging a segment of the segments of the input field displayed at positions on a screen by the display means and moving the segment in the screen; and
the input/display device one of minimizing and magnifying at least one of the segment and other segments on the screen according to movement of the segment dragged by the input means,
wherein said data identifier comprises an input device identifier that identifies an identity of an input operator,
wherein, when segments of an input field are displayed, segment labels are assigned to the segments according to a plurality of data identifiers previously specified to the respective segments,
wherein, in the storage, the data are stored after one of a depression of a lock button and an operation to explicitly close a medical report,
wherein said character comprises a letter,
wherein said data identifier comprises a screen identifier that identifies a screen where said input stroke information is stored, and
wherein in an operation to read data from said storage and to display the data, when an unchangeable state is beforehand set to the data, said input/display device displays an item indicating that the data cannot be changed.

10. The application method for supporting a medical treatment system in accordance with claim 1, wherein, in an operation to read data from said storage and to display the data, when an unchangeable state is beforehand set to the data, said input/display device displays an item indicating that the data cannot be changed.

11. The application method for supporting a medical treatment system in accordance with claim 1, further comprising:
the input means dragging a particular input field selected from a plurality of input fields displayed at particular positions on a screen by said display means and dropping the particular input field onto said sheet label; and
said storage storing data of said particular input field with a relationship established to said sheet label.

12. The application method for supporting a medical treatment system in accordance with claim 1, further comprising:
the input means moving in a horizontal direction in a sliding manner to cross an input field displayed at a position on a screen by the display means; and
the input/display device displaying the input field, the input field being subdivided into segments.

13. The application method for supporting a medical treatment system in accordance with claim 1, further comprising:
the input means dragging a segment on a screen by the display means and dropping the segment onto the sheet label; and
the storage storing data of the segment with a relationship established to the sheet label.

14. The application method for supporting a medical treatment system in accordance with claim 1, further comprising:
the input means moving from a first point to a second point on an image displayed at a position on a screen by the display means; and
the input/display device measuring a distance of movement between the first and the second points and displaying the distance over the image.

15. The application method for supporting a medical treatment system in accordance with claim 1, further comprising:
the input means is moving to draw a trace beginning at a point on an image displayed at a position on a screen by the display means; and
the input/display device rotating the image according to a length and a direction of the trace and displaying the rotated image.

16. The application method for supporting a medical treatment system in accordance with claim 1, further comprising:
the input means dragging an input field selected from a plurality of input fields displayed at positions on a screen by the display means and moving the input field in the screen; and the input/display device one of minimizing and magnifying one of the input field and other input fields on the screen according to movement of the input field dragged by the input means.

17. The application method for supporting a medical treatment system in accordance with claim 1, further comprising:
the input means dragging a segment of the segments of the input field displayed at positions on a screen by the display means and moving the segment in the screen; and
the input/display device one of minimizing and magnifying at least one of the segment and other segments on the screen according to movement of the segment dragged by the input means.

18. The application method for supporting a medical treatment system in accordance with claim 1, further comprising:
the input means dragging a sheet label displayed at positions on a screen by the display means and moving the sheet label upward; and
the input/display device reading data stored in the storage in relation to the sheet label from the storage and displaying the data below the sheet label based on the type of stored data.

19. The application method for supporting a medical treatment system in accordance with claim 1, wherein said data identifier comprises an input device identifier that identifies an identity of an input operator.

20. The application method for supporting a medical treatment system in accordance with claim 1, wherein said data identifier comprises a screen identifier that identifies a screen where said input stroke information is stored.

21. An application method for supporting a medical treatment system, the system comprising an input/display device, a storage, and a controller, said input/display device including input means and display means, said storage comprising a first database that stores a history of input stroke information automatically and a second database that stores explicit saving operations initiated by a user, said input stroke information comprising handwritten strokes, said controller comprising a display data generation controller, a storage data update controller, and a print data generation controller, the method comprising:
receiving said input stroke information by handwriting on said input/display device, said handwriting comprising directly touching a surface of said display means with said input means, said input/display device comprising a pen-tablet unit, said pen-tablet unit comprising said input means and said display means integrally combined, said input means comprising a pen-tablet pointer having a pen shape, said display means being one of a liquid-crystal display and a plasma display panel;
first storing said input stroke information in a vector representation in said storage using said display data generation controller;
displaying said input stroke information on said display using said display data generation controller;
first determining whether a data identifier has been received in said input stroke information, said storage data update controller performing said first determining such that if said data identifier is received in said input stroke information, then said first determining comprises:
searching for an intra-identifier code according to said data identifier and free input, said storage data update controller performing said searching; and
data-identifier recording said intra-identifier code, said storage data update controller performing said data-identifier recording;
free-input recording said free input, said storage data update controller performing said free-input recording;
enabling said user to save said intra-identifier code and said free input in said storage; second determining whether said intra-identifier code and said free input are saved in said storage, said second determining using said storage data update controller to control said second determining such that, if said intra-identifier code and said free input are not saved in said storage, a restoring operation is conducted, then said restoring operation comprises:
third determining whether a first change in said storage has occurred;
returning to said input/display device receiving said input stroke information to repeat said application method up to said second determining if said first change in said storage has occurred; and
first ending said application method if said first change in said storage has not occurred;
declaring a falsification of said intra-identifier code and said free input to be impossible if said restoring operation is not conducted;
fourth determining whether a second change in said storage has occurred;
second ending said application method if said second change in said storage has not occurred; and
if said second change in said storage has occurred, generating a copy of said storage without said intra-identifier code and said free input storage, recording said second change in said storage, and ending said application method,
wherein said method further comprises one of:
a first operation comprising the input means moving in a sliding manner on a sheet label displayed at a particular position on a screen by the display means, the input/display device reading, when the input means moves onto said sheet label, data stored in the storage in relation to said sheet label from the storage, and displaying the data by conducting a change-over operation for said sheet label;
a second operation comprising the input means dragging a particular input field selected from a plurality of input fields displayed at particular positions on a screen by the display means and dropping the particular input field onto said sheet label, and the storage storing data of said particular input field with a relationship established to said sheet label;
a third operation comprising the input means moving in a horizontal direction in a sliding manner to cross an input field displayed at a position on a screen by the display means, and the input/display device displaying the input field, the input field being subdivided into segments;
a fourth operation comprising the input means dragging a segment on a screen by the display means and dropping the segment onto said sheet label, and the storage storing data of the segment with a relationship established to said sheet label;
a fifth operation comprising the input means moving from a first point to a second point on an image displayed at a position on a screen by the display means, and the input/display device measuring a distance of movement between the first and the second points and displaying the distance over the image; and a sixth operation comprising the input means moving to draw a trace beginning at a point on an image displayed at a position on a screen by the display means, and the input/display device rotating the image according to a length and a direction of the trace and displaying the rotated image.

22. The application method for supporting a medical treatment system in accordance with claim 21, wherein, when segments of an input field are displayed, segment labels are assigned to the segments according to a plurality of data identifiers previously specified to the respective segments.

23. The application method for supporting a medical treatment system in accordance with claim 22, further comprising:
conducting character recognition processing of said receiving of said input stroke information to determine if a character is received in said input stroke information,
wherein said input/display device conducts said character recognition processing for said input stroke information inputted from said input means and comprising an array of values of coordinates, converts by said character recognition processing said input stroke information into text data including an array of character codes, and displays the text data.

24. The application method for supporting a medical treatment system in accordance with claim 23, wherein in an operation to read data from said storage and to display the data, when an unchangeable state is beforehand set to the data, said input/display device displays an item indicating that the data cannot be changed.

25. The application method for supporting a medical treatment system in accordance with claim 23, wherein said method further comprises said first operation, said second operation, said third operation, said fourth operation, said fifth operation, and said sixth operation,
wherein, when segments of an input field are displayed, segment labels are assigned to the segments according to identifiers previously specified to the respective segments,
wherein, in an operation to read data from said storage and to display the data, when an unchangeable state is beforehand set to the data, said input/display device displays an item indicating that the data cannot be changed,
wherein said character comprises a letter,
wherein said data identifier comprises a screen identifier that identifies a screen where said input stroke information is stored, and
wherein said data identifier comprises an input device identifier that identifies an identity of an input operator.

26. The application method for supporting a medical treatment system in accordance with claim 25, wherein said method further comprises:
a seventh operation comprising the input means dragging an input field selected from a plurality of input fields displayed at positions on a screen by the display means and moving the input field in the screen, and the input/display device one of minimizing and magnifying one of the input field and other input fields on the screen according to movement of the input field dragged by the input means;
an eighth operation comprising the input means dragging a segment of the segments of the input field displayed at positions on a screen by the display means and moving the segment in the screen, and the input/display device one of minimizing and magnifying at least one of the segment and other segments on the screen according to movement of the segment dragged by the input means; and
a ninth operation comprising the input means dragging a sheet label displayed at positions on a screen by the display means and moving the sheet label upward, and the input/display device reading data stored in the storage in relation to the sheet label from the storage and displaying the data below the sheet label based on the type of stored data.

27. The application method for supporting a medical treatment system in accordance with claim 22, wherein in an operation to read data from said storage and to display the data, when an unchangeable state is beforehand set to the data, said input/display device displays an item indicating that the data cannot be changed.

28. The application method for supporting a medical treatment system in accordance with claim 21, wherein, in an operation to read data from said storage and to display the data, when an unchangeable state is beforehand set to the data, said input/display device displays an item indicating that the data cannot be changed.

29. The application method for supporting a medical treatment system in accordance with claim 21, said method further comprising one of:
a seventh operation comprising the input means dragging an input field selected from a plurality of input fields displayed at positions on a screen by the display means and moving the input field in the screen, and the input/display device one of minimizing and magnifying one of the input field and other input fields on the screen according to movement of the input field dragged by the input means;
an eighth operation comprising the input means dragging a segment of the segments of the input field displayed at positions on a screen by the display means and moving the segment in the screen, and the input/display device one of minimizing and magnifying at least one of the segment and other segments on the screen according to movement of the segment dragged by the input means; and
a ninth operation comprising the input means dragging a sheet label displayed at positions on a screen by the display means and moving the sheet label upward, and the input/display device reading data stored in the storage in relation to the sheet label from the storage and displaying the data below the sheet label based on the type of stored data.

30. The application method for supporting a medical treatment system in accordance with claim 21, wherein said data identifier comprises an input device identifier that identifies an identity of an input operator.

31. The application method for supporting a medical treatment system in accordance with claim 21, wherein said data identifier comprises a screen identifier that identifies a screen where said input stroke information is stored.

32. A medical treatment support system comprising:
an input-display device comprising a pen-tablet unit, said pen-tablet unit comprising an input means and a display means integrally combined, said input means comprising a pen-tablet pointer having a pen shape, said input means for receiving input stroke information by handwriting, said input stroke information comprising handwritten strokes, said handwriting comprising directly touching a surface of said display means with said input means, said display means being one of a liquid-crystal display and a plasma display panel;

a storage comprising:
- a first database that stores a history of said input stroke information automatically; and
- a second database that stores explicit saving operations initiated by a user;

a controller comprising a display data generation controller, a storage data update controller, and a print data generation controller;

a first input stroke information storing module for a first storing of said input stroke information in a vector representation in said storage using said display data generation controller;

an input stroke information displaying module for displaying said input stroke information on said display using said display data generation controller;

means for first determining whether a data identifier has been received in said input stroke information, said means for first determining comprising said storage data update controller that performs said first determining such that if said data identifier is received in said input stroke information, an intra-identifier code searching module of said means for first determining searches for an intra-identifier code according to said data identifier and free input, said storage data update controller performing said searching, and a data-identifier intra-identifier code recording module for data-identifier recording said intra-identifier code, said storage data update controller performing said data-identifier recording;

means for conducting character recognition processing of said receiving said input stroke information to determine if a character has been received in said input stroke information;

a free-input recording module for recording said free input, said storage data update controller performing said free-input recording;

a user enabling module for enabling said user to save said intra-identifier code and said free input in said storage substantially all as medical data;

means for second determining whether said intra-identifier code and said free input are saved in said storage, said second determining means using said storage data update controller to control said second determining such that, if said intra-identifier code and said free input are not saved in said storage, then a restoring operation conducting module is implemented to conduct a restoring operation, said restoring operation conducting module comprising:
- means for third determining whether a first change in said storage has occurred;
- an input/display device receiving returning module for returning to said input/display device to receive said input stroke information if said first stage in said storage has occurred; and
- a first ending module for ending use of said medical treatment support system;

a falsification declaring module for declaring a falsification of said intra-identifier code and said free input to be impossible if said restoring operation is not conducted;

means for fourth determining whether a second change in said storage has occurred;

a second ending module for ending use of said medical treatment support system if said second change in said storage has not occurred; and a copy-generating, second-change recording module for generating a copy of said storage without said intra-identifier code and said free input storage, recording said second change in said storage, and ending use of said medical treatment support system if said second change in said storage has occurred, wherein the input means drags a particular input field selected from a plurality of input fields displayed at particular positions on a screen by said display means and drops the particular input field onto a sheet label, and wherein said storage stores data of said particular input field with a relationship established to said sheet label.

33. The medical treatment support system claimed in claim 32, wherein data in the storage is stored after one of a depression of a lock button and an operation to explicitly close a medical report.

34. The medical treatment support system claimed in claim 32, wherein said data identifier comprises an input device identifier that identifies an identity of an input operator.

35. The medical treatment support system claimed in claim 32, wherein said data identifier comprises a screen identifier that identifies a screen where said input stroke information is stored.

* * * * *